United States Patent [19]
Boneau

[11] Patent Number: 5,891,190
[45] Date of Patent: Apr. 6, 1999

[54] ENDOVASCULAR SUPPORT DEVICE AND METHOD

[76] Inventor: Michael D. Boneau, 342 W. Sunnyoaks, Campbell, Calif. 95008

[21] Appl. No.: 471,738

[22] Filed: Jun. 6, 1995

Related U.S. Application Data

[62] Division of Ser. No. 172,420, Dec. 22, 1993, abandoned, which is a division of Ser. No. 398,180, Aug. 24, 1989, Pat. No. 5,292,331.

[51] Int. Cl.$^6$ ......................................................... A61F 2/06
[52] U.S. Cl. .................................................. 623/1; 623/12
[58] Field of Search ................... 623/1, 11, 12; 606/194, 195; 600/36

[56] References Cited

U.S. PATENT DOCUMENTS

| | | |
|---|---|---|
| 4,733,665 | 3/1988 | Palmaz . |
| 4,739,762 | 4/1988 | Palmaz . |
| 4,776,337 | 10/1988 | Palmaz . |
| 4,886,062 | 12/1989 | Wiktor ......................................... 623/1 |
| 5,035,706 | 7/1991 | Gianturco et al. ....................... 606/198 |
| 5,102,417 | 4/1992 | Palmaz . |
| 5,507,767 | 4/1996 | Maeda et al. .............................. 623/12 |
| 5,507,768 | 4/1996 | Lam ............................................ 623/1 |
| 5,549,635 | 8/1996 | Solar ........................................... 623/1 |
| 5,556,413 | 9/1996 | Lam ........................................... 623/1 |
| 5,562,728 | 10/1996 | Lazarus et al. ............................. 623/1 |
| 5,569,295 | 10/1996 | Lam ........................................... 623/1 |
| 5,591,198 | 1/1997 | Boyle et al. ................................ 623/1 |

*Primary Examiner*—Debra S. Brittingham
*Attorney, Agent, or Firm*—Richard L. Klein

[57] ABSTRACT

An endovascular support device for treatment of chronic restenosis or other vascular narrowing is disclosed together with a method of manufacture and a method for delivering a plurality of such devices to an affected area of a vessel. In a preferred embodiment, the endovascular support device comprises a unitary wire-like structure configured to form a plurality of upper and lower peaks which may be compressed for delivery to an affected area of a coronary or peripheral vessel in a human, and then expanded to maintain a passageway through the vessel.

8 Claims, 3 Drawing Sheets

ENDOVASCULAR SUPPORT DEVICE AND METHOD

This is a division of application Ser. No. 08/172,420, filed Dec. 22, 1993 now abandoned, which is a division of application Ser. No. 07/398,180, filed Aug. 24, 1989, now U.S. Pat. No. 5,292,331.

FIELD OF THE INVENTION

The present invention relates generally to medical devices, and particularly relates to implantable devices for treating narrowing of coronary or peripheral vessels in humans.

BACKGROUND OF THE INVENTION

Cardiovascular disease, including atherosclerosis, is the leading cause of death in the U.S. The medical community has developed a number of methods for treating coronary heart disease, some of which are specifically designed to treat the complications resulting from atherosclerosis and other forms of coronary arterial narrowing.

The most impelling development in the past decade for treating atherosclerosis and other forms of coronary narrowing is percutaneous transluminal coronary angioplasty, hereinafter referred to simply as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions and is related to the nature of the plaque. Soft, fatty plaque deposits are flattened by the balloon and hardened deposits are cracked and split to enlarge the lumen. The wall of the artery itself is also stretched when the balloon is inflated.

PTCA is performed as follows: A thin-walled, hollow guiding catheter is typically introduced into the body via a relatively large vessel, such as the femoral artery in the groin area or the brachial artery in the arm. Access to the femoral artery is achieved by introducing a large bore needle directly into the femoral artery, a procedure known as the Seldinger Technique. Once access to the femoral artery is achieved, a short hollow sheath is inserted to maintain a passageway during PTCA. The flexible guiding catheter, which is typically polymer coated, and lined with Teflon, is inserted through the sheath into the femoral artery. The guiding catheter is advanced through the femoral artery into the iliac artery and into the ascending aorta. Further advancement of the flexible catheter involves the negotiation of an approximately 180 degree turn through the aortic arch to allow the guiding catheter to descend into the aortic cusp where entry may be gained to either the left or the right coronary artery, as desired.

After the guiding catheter is advanced to the ostium of the coronary artery to be treated by PTCA, a flexible guidewire is inserted into the guiding catheter through a balloon and advanced to the area to be treated. The guidewire provides the necessary steerability for lesion passage. The guidewire is advanced across the lesion, or "wires" the lesion, in preparation for the advancement of a polyethylene, polyvinyl chloride, polyolefin, or other suitable substance balloon catheter across the guide wire. The balloon, or dilatation, catheter is placed into position by sliding it along the guide wire. The use of the relatively rigid guide wire is necessary to advance the catheter through the narrowed lumen of the artery and to direct the balloon, which is typically quite flexible, across the lesion. Radiopaque markers in the balloon segment of the catheter facilitate positioning across the lesion. The balloon catheter is then inflated with contrast material to permit fluoroscopic viewing during treatment. The balloon is alternately inflated and deflated until the lumen of the artery is satisfactorily enlarged.

Unfortunately, while the affected artery can be enlarged, in some instances the vessel restenoses chronically, or closes down acutely, negating the positive effect of the angioplasty procedure. In the past, such restenosis has frequently necessitated repeat PTCA or open heart surgery. While such restenosis does not occur in the majority of cases, it occurs frequently enough that such complications comprise a significant percentage of the overall failures of the PTCA procedure, for example, twenty-five to thirty-five percent of such failures.

To lessen the risk of restenosis, various devices have been proposed for mechanically keeping the affected vessel open after completion of the angioplasty procedure. Such mechanical endoprosthetic devices, which are generally referred to as stents, are typically inserted into the vessel, positioned across the lesion, and then expanded to keep the passageway clear. Effectively, the stent overcomes the natural tendency of the vessel walls of some patients to close back down, thereby maintaining a more normal flow of blood through that vessel than would be possible if the stent were not in place.

Various types of stents have been proposed, although to date none has proven satisfactory. One proposed stent involves a tube of stainless wire braid. During insertion, the tube is positioned along a delivery device, such as a catheter, in extended form, making the tube diameter as small as possible. When the stent is positioned across the lesion, it is expanded, causing the length of the tube to contract and the diameter to expand. Depending on the materials used in construction of the stent, the tube maintains the new shape either through mechanical force or otherwise. For example, one such stent is a self-expanding stainless steel wire braid. Other forms of stents include various types tubular metallic cylinders expanded by balloon dilatation. One such device is referred to as the Palmaz stent, discussed further below.

Another form of stent is a heat expandable device. This device, originally designed using NITINOL by Dotter has recently been modified to a new tin-coated, heat expandable coil by Regan. The stent is delivered to the affected area on a catheter capable of receiving heated fluids. Once properly positioned, heated saline is passed through the portion of the catheter on which the stent is located, causing the stent to expand. Numerous difficulties have been encountered with this device, including difficulty in obtaining reliable expansion, and difficulties in maintaining the stent in its expanded state.

Perhaps the most popular stent presently under investigation in the United States is referred to as the Palmaz stent. The Palmaz stent involves what may be thought of as a stainless steel cylinder having a number of slits in its circumference, resulting in a mesh when expanded. The stainless steel cylinder is delivered to the affected area by means of a balloon catheter, and is then expanded to the proper size by inflating the balloon.

Significant difficulties have been encountered with all prior art stents. Each has its percentage of thrombosis, restenosis and tissue in-growth, as well as varying degrees of difficulty in deployment. Another difficulty with at least some of prior art stents is that they do not readily conform to the vessel shape. In addition, the relatively long length of such prior art stents has made it difficult to treat curved vessels, and has also effectively prevented successful implantation of multiple such stents. Anticoagulants have historically been required at least for the first three months after placement. These and other complications have resulted in a low level of acceptance for such stents within the medical community, and to date stents have not been accepted as a practical method for treating chronic restenosis.

Thus there has been a long felt need for a stent which is effective to maintain a vessel open, without resulting in significant thrombosis, which may be easily delivered to the affected area, easily expanded to the desired size, easily conformed to the affected vessel, and easily used in multiples to treat curved vessels and varying lengths of lesions.

SUMMARY OF THE INVENTION

The present invention substantially reduces the complications and overcomes the limitations of the prior art devices. The endovascular support device of the present invention comprises a device having very low mass which is capable of being delivered to the affected area by means of a slightly modified conventional balloon catheter similar to that used in a standard balloon angioplasty procedure.

The support device of the present invention may then be expanded by normal expansion of the balloon catheter used to deliver the stent to the affected area, and its size can be adjusted within a relatively broad range in accordance with the diagnosis of the treating physician.

Because of the range of diameters through which the support device of the present invention may be expanded, it may be custom expanded to the specific lesion diameter, and is readily conformable to the vessel shape. In addition, a plurality of support devices of the present invention may be readily implanted in a number commensurate with the length of the lesion under treatment. As a result, curved or "S" shaped vessels may be treated.

The stent, or endovascular support devise, of the present invention may preferably be comprised of implantable quality high grade stainless steel, machined specially for intravascular applications. The support device may comprise, in effect, a metal circle or ellipsoid formed to create a plurality of axial bends, thereby permitting compression of the stent onto a delivery catheter, and subsequent expansion once in place at the affected area.

It is one object of the present invention to provide a stent which substantially overcomes the limitations of the prior art.

It is a further object of the present invention to provide a stent capable of being implanted simply and reliably.

Another object of the present invention is to provide a stent which does not result in significant thrombosis at the point of implant.

Yet another object of the present invention is to provide a stent which can be selectively sized in accordance with the anatomic configuration dictated by the lesion itself.

A still further object of the present invention is to provide a method for supplying an endovascular support device which permits a plurality of such devices to be implanted commensurate with the length of the lesion under treatment.

These and other objects of the present invention can be better appreciated from the following detailed description of the invention, taken in conjunction with the attached drawings.

FIGURES

Figure 5:
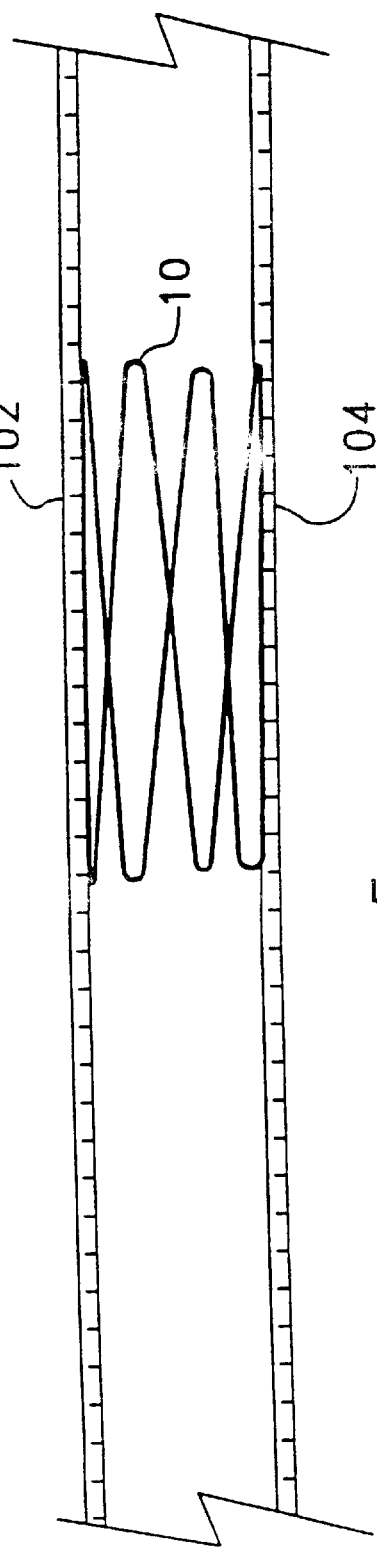

FIG. 5 snows a support device of the present invention in its expanded form within a sectioned portion of a lesion after removal of the balloon catheter.

Figure 6B:
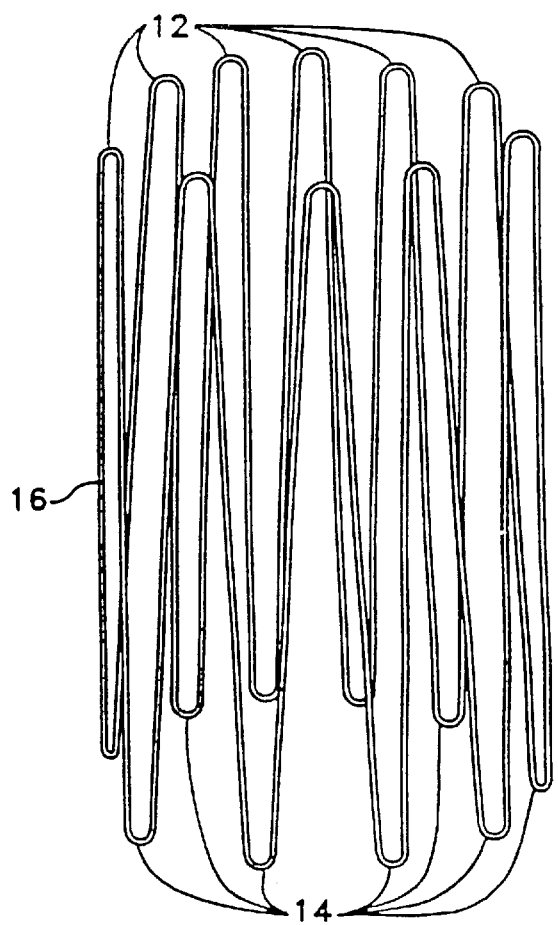
Figure 6A:
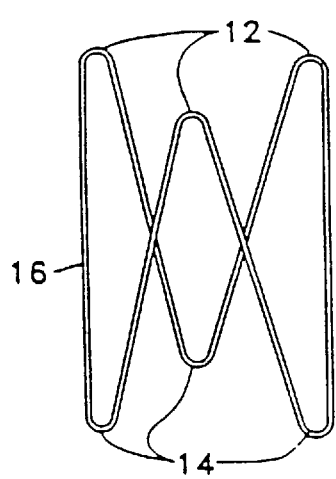

FIGS. 6a–b show alternative configurations of a support device according to the present invention.

DETAILED DESCRIPTION OF THE INVENTION

Figure 1:
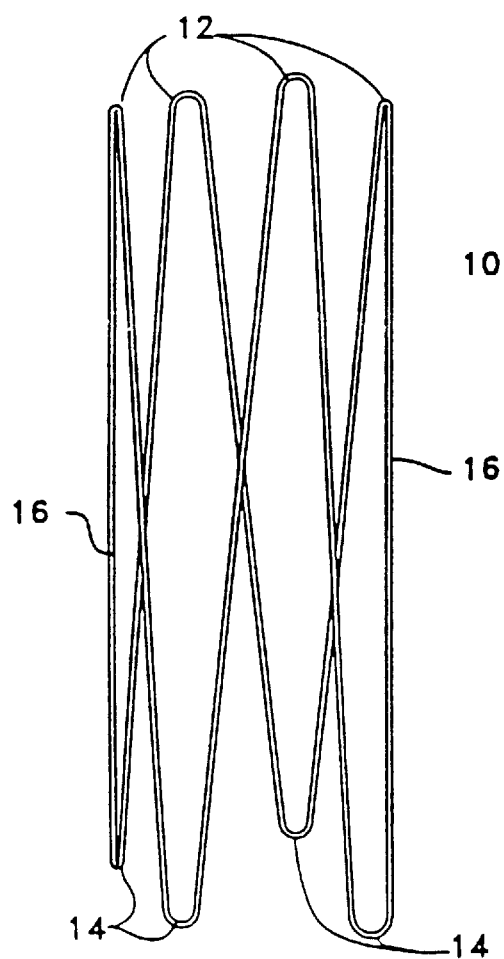
FIG. 1 shows a perspective view of an endovascular support device constructed according to the present invention, in its expanded form.

Referring first to FIG. 1, an endovascular support device 10, referred to hereinafter more conveniently as a stent, constructed in accordance with the present invention can be seen in perspective view. The stent 10 of FIG. 1 is shown in its expanded form, prior to compression over a suitable delivery system as discussed in detail hereinafter.

In a preferred embodiment, the stent 10 comprises a single piece of material, bent to form a plurality of upper axial turns 12 and lower axial turns 14. In the embodiment shown in FIG. 1, four upper turns 12 are connected to the four lower turns 14 by substantially straight segments 16. The axial turns 12 and 14 can be seen to permit the stent 10 to be compressed or expanded over a wide range while still maintaining significant mechanical force, such as required to prevent a vessel from restenosing. While a preferred embodiment comprises a single piece of material, in some instances a suitably welded wire may be acceptable.

It will be appreciated that the number turns 12 and 14 can vary over a reasonably wide range, defined as "N" number of turns" and may in fact vary between two and ten such turns or peaks. However, it is currently believed that the optimum number of turns or peaks will range between three and five for most applications, and particularly for cardiovascular applications.

The stent 10 is preferably constructed of implantable materials having good mechanical strength. An embodiment which has proven successful in preliminary testing is machined from 316LSS implantable quality stainless steel bar stock. The bar stock is machined to form substantially a toroid, which is then acid etched in phosphoric and sulfuric acid at approximately 180° to 185° to break the edges. The etched toroid is then plated with copper to avoid galling and to provide lubricity.

The copper plated toroid is then bent to the shape of the stent 10 shown in FIG. 1, after which the copper plating is stripped from the stent. The stent is then returned to the acid bath to reduce the wire size to the desired diameter, which is in the range of 0.002" to 0.025". It is presently believed that the optimum wire size for the final product is in the range of 0.008" to 0.009'. It will be appreciated that the strength of the stent—that is, its ability to prevent restenosis—is inversely proportional to the number of peaks or turns in the stent, so that stents having a greater number of turns will typically be formed of larger wire diameters. Finally, although not required in all cases, the outside of the stent may be selectively plated with platinum to provide improved visibility during fluoroscopy. The cross-sectional shape of the finished stent may be circular, ellipsoidal, rectangular, hexagonal, square, or other polygon, although at present it is believed that circular or ellipsoidal may be preferable.

The minimum length of the stent, or the distance between the upper turns 12 and lower turns 14, is determined in large measure by the size of the vessel into which the stent will be implanted. The stent 10 will preferably be of sufficient length as to maintain its axial orientation within the vessel without shifting under the hydraulics of blood flow (or other fluid flow in different types of vessels), while also being long enough to extend across a, least a significant portion of the affected area. At the same time, the stent should be short enough as to not introduce unnecessarily large amounts of material as might cause undue thrombosis. Typical cardiovascular vessels into which the stent 10 might be implanted range from 1.5 millimeters to five millimeters in diameter, and corresponding stents may range from one millimeter to two centimeters in length. However, in most instances the stent will range in length between 3.5 millimeters and 6 millimeters. Preliminary testing of stents having a length between 3.5 millimeters and 4.5 millimeters has been performed with good success outside the United States, and testing on animals is also ongoing.

Figure 2:
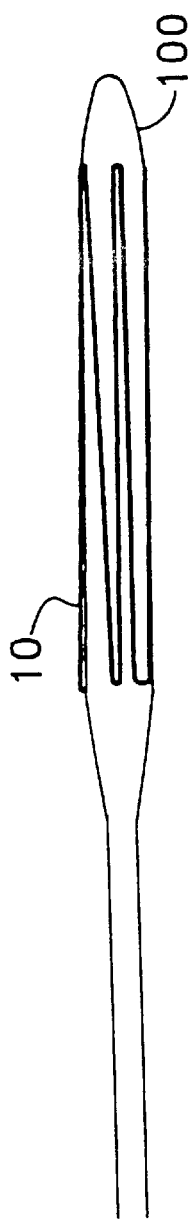
FIG. 2 shows a support device constructed according to the present invention and compressed onto a balloon catheter.

Once the wire size of the stent 10 has been reduced to the desired size, the stent 10 may be crimped onto a balloon 100, as shown in FIG. 2, for delivery to the affected region 102 of a vessel 104 such as a coronary artery. For the sake of simplicity, the multiple layers of the vessel wall 104 are shown as a single layer, although it will be understood by those skilled in the art that the lesion typically is a plaque deposit within the intima of the vessel 104.

One suitable balloon for delivery of the stent 10 is manufacturers by Advanced Cardiovascular Systems, Inc., of Santa Clara, Calif. ("ACS"), and is eight millimeters in length with Microglide® on the shaft only. The stent-carrying balloon 100 is then advanced to the affected area and across the lesion 102 in a conventional manner, such as by use of a guide wire and a guide catheter (not shown). A suitable guide wire is the 0.014" Hi Torque Floppy manufactured by ACS, and a suitable guiding catheter is the ET0.076 lumen guide catheter, also manufactured by ACS.

Figure 3:
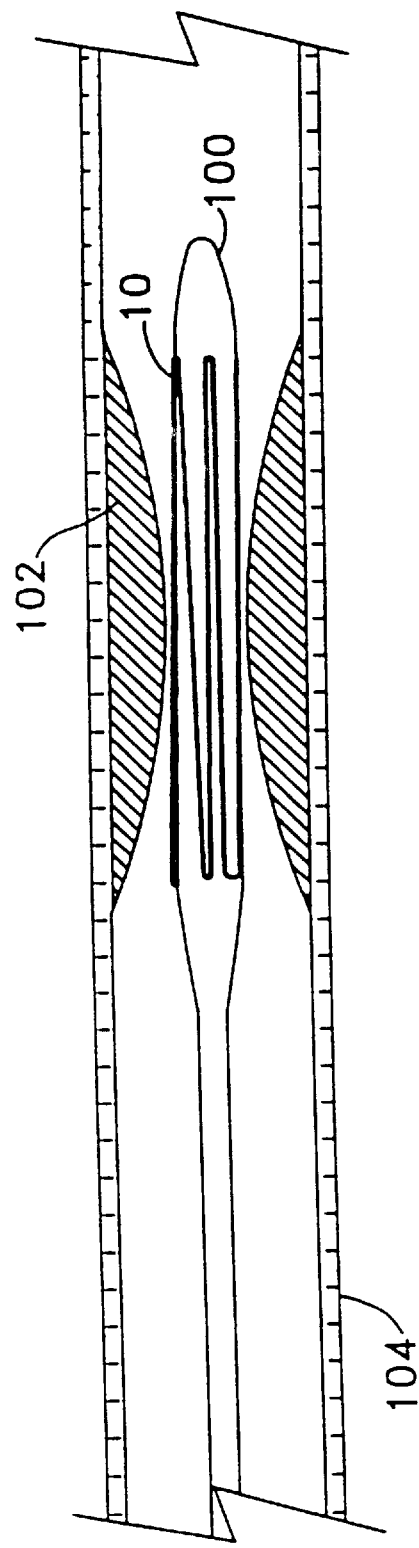
FIG. 3 shows a support device compressed onto a balloon catheter as shown in FIG. 2, and positioned within a sectioned portion of an affected area of a artery or other vessel.

Once the balloon 100 is in place across the lesion 102, as shown in FIG. 3, the balloon 100 may be inflated, again substantially in a conventional manner. In selecting a balloon, it is helpful to ensure that the balloon will provide radially uniform inflation so that the stent 10 will expand equally along each of the peaks. The inflation of the balloon 100, shown in FIG. 4, causes the expansion of the stent 10 from its crimped configuration back to a shape substantially like that shown in FIG. 1. The amount of inflation, and commensurate amount of expansion of the stent 10, may be varied as dictated by the lesion itself, making the stent of the present invention particularly flexible in the treatment of chronic restenosis.

Figure 4:
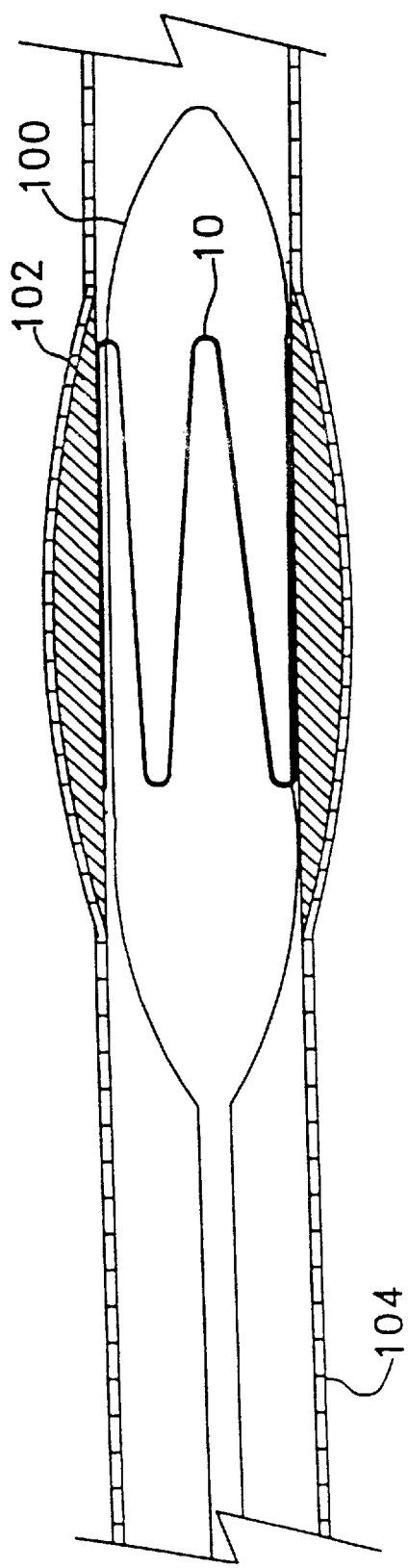
FIG. 4 shows a support device according to the present invention in its expanded form within a sectioned portion of a vessel including a lesion.

Because of the inflation of the balloon, the lesion 102 in the vessel 104 is expanded, and causes the arterial wall of the vessel 104 to bulge radially, as simplistically depicted in FIG. 4. At the same time, the plaque deposited within the intima of the vessel is displaced and thinned, and the stent 10 is embedded in the plaque or other fibrotic material adhering to the intima of the vessel 104.

Following inflation of the balloon 100 and expansion of the stent 10 within the vessel 104, the balloon is deflated and removed. The exterior wall of the vessel 104 returns to its original shape through elastic recoil. The stent 10, however, remains in its expanded form within the vessel, and prevents further restenosis of the vessel. The stent maintains an open passageway through the vessel, as shown in FIG. 4, so long as the tendency toward restenosis is not greater than the mechanical strength of the stent 10. Because of the low mass of the support device 10 of the present invention, thrombosis is less likely to occur. Ideally, the displacement of the plaque deposits and the implantation of the stent 10 will result in a smooth inside diameter of the vessel 104, although this ideal cannot be achieved in all cases.

One of the advantages of the stent "M" 10 is that multiple stents may be used in the treatment of a single lesion. Thus, for example, in the event the affected area shown in FIGS. 3 and 4 was longer than the stent 10, additional stents 10 could be positioned elsewhere along the lesion to prevent restenosis. In preliminary testing, up to four stents have been used successfully along a single lesion. Due to the conformability of the stent 10, not only can varying lesion lengths be treated,but curved vessels and "S" shaped vessels may also be treated by the present invention. In instances where it is known in advance that multiple stents will be the preferred method of treatment, a plurality of such stents, "M" number of stents may be positioned along a single balloon catheter for simultaneous delivery to the affected area.

As discussed above, the number of peaks or turns 12 and 14 in the stent 10 "N" number of turns may vary between two and ten. To this end, shown in FIGS. 6a and 6b are two alternative configurations of the stent 10. The alternative embodiment shown in 6a can be seen to have three upper and three lower peaks or turns, while the embodiment shown in FIG. 6b can be seen to have ten upper and ten lower peaks.

While the primary application for the stent 10 is presently believed to be treatment of cardiovascular disease such as atherosclerosis or other forms off coronary narrowing, the stent 10 of the present invention may also be used for treatment of narrowed vessels in the kidney, leg, carotid, or elsewhere in the body. In such other vessels,the size of the stent may need to be adjusted to compensate for the differing sizes of the vessel to be treated, bearing in mind the sizing guidelines provided above.

Having fully described a preferred embodiment of the invention, those skilled in the art will immediately appreciate, given the teachings herein, that numerous alternatives and equivalents exist which do not depart from the present invention. It is therefore to be understood that the present invention is not to be limited by the foregoing description, but only by the appended claims.

I claim:

1. A method for treating narrowing of vessels within humans comprising the steps of
   providing a plurality of stents, each stent comprising a unitary wire-like circular member bent to form a plurality of N substantially straight, non-overlapping segments wherein each segment is connected end to end with the adjacent segments, the stent further being capable of being compressed mechanically to maintain a reduced volume and thereafter expanded,
   compressing each of the plurality of stents onto a balloon catheter,
   advancing the balloon catheter and the plurality of stents to an area of the vessel, and
   inflating the balloon catheter to expand the plurality of stents within the area of the vessel.

2. The method of claim 1 wherein the stents are not connected to one another.

3. A method for treating narrowing of vessels within humans comprising the steps of:

providing at least one endovascular support device, each of the at least one endovascular support device comprising a continuous stent member formed of a plurality of substantially straight segments connected by axial bends, the substantially straight segments formed without interconnection or joining of the substantially straight segments intermediate of the axial bends;

compressing the at least one endovascular support device onto a balloon of a balloon catheter;

advancing the balloon catheter and the at least one endovascular support device to an affected area of a vessel;

inflating the balloon to expand the at least one endovascular support device within the affected area of the vessel.

4. The method of claim 3 wherein the at least one endovascular support comprises at least two endovascular support devices.

5. The method of claim 4 wherein the at least two endovascular support devices are not connected to one another.

6. A method for treating narrowing of vessels within humans comprising the steps of:

providing at least one endovascular support device, each of the at least one endovascular support device formed of a plurality of N substantially straight segments wherein each segment has a first end and a second end, and the first end of the first segment is connected to the first end of the second segment, the second end of the second segment is connected to the second end of the third segment, the first end of the the third segment is connected to the first end of the fourth segment, and so on until the second end of the Nth segment is connected to the second end of the first segment;

compressing the at least one endovascular support device onto a balloon of a balloon catheter;

advancing the balloon catheter and the at least one endovascular support device to an affected area of a vessel;

inflating the balloon to expand the at least one endovascular support within the affected area of the vessel.

7. The method of claim 6 wherein the at least one endovascular support comprises at least two endovascular support devices.

8. The method of claim 7 wherein the at least two endovascular support devices are not connected to one another.

\* \* \* \* \*